US007771403B2

(12) United States Patent
Roy

(10) Patent No.: US 7,771,403 B2
(45) Date of Patent: Aug. 10, 2010

(54) UNIFORM FEED CONNECTOR FOR DEVICES FOR THE DELIVERY OF ACTIVE PRINCIPLES

(75) Inventor: Pierre Roy, Paris (FR)

(73) Assignee: Eyegate Pharma S.A., Paris (FR)

( * ) Notice: Subject to any disclaimer, the term of this patent is extended or adjusted under 35 U.S.C. 154(b) by 525 days.

(21) Appl. No.: 10/548,210

(22) PCT Filed: Mar. 3, 2004

(86) PCT No.: PCT/IB2004/001208

§ 371 (c)(1), (2), (4) Date: Sep. 1, 2005

(87) PCT Pub. No.: WO2004/078093

PCT Pub. Date: Sep. 16, 2004

(65) Prior Publication Data

US 2006/0229590 A1 Oct. 12, 2006

(30) Foreign Application Priority Data

Mar. 3, 2003 (FR) .................................. 03 02549

(51) Int. Cl.
*A61M 35/00* (2006.01)
*A61M 39/00* (2006.01)
*B65B 3/04* (2006.01)

(52) U.S. Cl. ......................... 604/295; 604/298; 141/21; 141/84; 141/383

(58) Field of Classification Search ................. 141/286, 141/21, 22, 84, 383; 604/535, 294, 295, 604/298

See application file for complete search history.

(56) References Cited

U.S. PATENT DOCUMENTS

| | | | | |
|---|---|---|---|---|
| 5,543,042 | A | 8/1996 | Filan et al. | |
| 5,609,584 | A * | 3/1997 | Gettig et al. | 604/535 |
| 5,685,845 | A * | 11/1997 | Grimard | 604/82 |
| 5,873,872 | A * | 2/1999 | Thibault et al. | 604/414 |
| 6,154,671 | A * | 11/2000 | Parel et al. | 604/20 |
| 6,183,465 | B1 * | 2/2001 | Meier et al. | 604/535 |
| 6,341,802 | B1 * | 1/2002 | Matkovich | 604/198 |
| 6,511,472 | B1 * | 1/2003 | Hayman et al. | 604/533 |
| 6,536,805 | B2 * | 3/2003 | Matkovich | 604/198 |
| 6,681,946 | B1 * | 1/2004 | Jansen et al. | 141/329 |
| 6,955,669 | B2 * | 10/2005 | Curutcharry | 604/415 |
| 6,957,745 | B2 * | 10/2005 | Thibault et al. | 141/330 |
| 7,252,308 | B2 * | 8/2007 | Thilly | 604/403 |
| 2004/0079438 | A1 * | 4/2004 | Bruna et al. | 141/21 |
| 2006/0169348 | A1 * | 8/2006 | Yigal | 141/21 |

FOREIGN PATENT DOCUMENTS

| | | |
|---|---|---|
| EP | 0761562 | 3/1997 |
| EP | 1201265 | 5/2002 |
| FR | 2773320 | 7/1990 |
| WO | WO 02/085429 | 10/2002 |

* cited by examiner

*Primary Examiner*—Gregory L Huson
*Assistant Examiner*—Nicolas A Arnett
(74) *Attorney, Agent, or Firm*—Foley & Lardner LLP; Michel Morency

(57) ABSTRACT

The feed connector (270) capable of interacting with a device for delivering active principles comprising a reservoir delimited by at least two lateral walls of substantially cylindrical shape and extending opposite one another, is characterized in that it includes means (202, 203, 204, 205) for dispensing active principles into the reservoir that are arranged such that said reservoir is filled substantially uniformly between the two lateral walls.

21 Claims, 5 Drawing Sheets

UNIFORM FEED CONNECTOR FOR DEVICES FOR THE DELIVERY OF ACTIVE PRINCIPLES

The present patent application is a non-provisional application of International Application No. PCT/IB2004/001208, filed Mar. 3, 2004.

FIELD OF THE INVENTION

The invention relates to systems for dispensing active principles into a reservoir of a device for delivering such active principles.

BACKGROUND OF THE INVENTION

For example, document FR 2 773 320 describes an apparatus for delivering active principles by iontophoresis, more particularly via the ocular and/or transcleral route. This device includes an annular reservoir capable of being applied to the ocular tissue at the periphery of the cornea of an eyeball and capable of receiving active principles to be transferred through these ocular tissues by iontophoresis. The active principles are for treating infections or disorders of the intraocular tissues (conjunctiva, cornea, sclera, iris, crystalline, ciliary body, choroid, retina, optic nerve). Active principles are understood to mean anti-inflammatories, antibiotics, anti-virals, anti-fungals, anti-cancer medicinal products, anti-angiogenesis products, anti-glaucoma products, neuroprotectors and, generally speaking, any type of medicinal product for caring for the eye.

The reservoir of this delivery apparatus is fed with active principles by means of a supply tube located at one point in the reservoir. The drawback of this feed system is its lack of symmetry, which assumes that the active principle injected is sufficiently fluid for it to be able to be distributed relatively uniformly in said reservoir. In the case of an active principle having a degree of viscosity, it is necessary to inject the solution slowly in order to obtain good distribution. In addition, the evacuation of air may pose a problem.

An object of the invention is to provide a system for dispensing active principles into a reservoir of a delivery device allowing the transfer of a fluid from any receptacle, enabling the above-mentioned problems to be solved.

BRIEF DESCRIPTION OF THE INVENTION

To that end, according to the invention, provision is made for a feed connector capable of interacting with a device for delivering active principles comprising a reservoir delimited by at least two lateral walls of substantially cylindrical shape and extending opposite one another, the feed connector also including means for dispensing active principles into the reservoir that are arranged such that said reservoir is filled substantially uniformly between the two lateral walls.

Advantageously, but optionally, the connector has at least one of the following characteristics:

- the dispensing means comprise distribution means capable of distributing the active principles substantially uniformly before they arrive in said reservoir;
- the distribution means have two plates spaced apart from one another and extending opposite one another, thereby delimiting a space for distribution of the active products;
- the plates are held apart and secured to one another by means forming a spacer;
- the dispensing means are capable of filling the reservoir substantially radially through orifices made in one of the two lateral walls;
- the dispensing means comprise a conduit for supplying the active principles;
- it also includes means for connection with a receptacle containing the active principles for filling the reservoir;
- the connection means are arranged such that, once the connection has been made between the receptacle and the connector, said connection is practically irreversible;
- it also includes locking means capable of locking said connector in place once said connector is interacting with the device for delivering active principles;
- the locking means are arranged so as to be practically disengaged during filling of said reservoir;
- the locking means include at least one catching tongue capable of deforming elastically;
- the locking means include at least one stud extending as a projection from the catching tongue and capable of interacting with an orifice made in the delivery device;
- the locking means are arranged so as to be disengaged when the connection with the receptacle containing the principles is made; and
- the dispensing means are arranged such that a ratio of a dead volume of the connector to a volume of the reservoir is minimal.

The invention also provides a device for delivering active principles comprising a reservoir delimited by at least two lateral walls of substantially cylindrical shape and extending opposite one another, and also including a feed connector having at least one of the preceding characteristics.

BRIEF DESCRIPTION OF THE DRAWINGS

Other characteristics and advantages of the invention will become apparent from the following description of a preferred embodiment and variants. In the appended drawings.

DETAILED DESCRIPTION OF THE INVENTION

We will illustrate the invention by describing below a preferred embodiment and variants applied to an annular reservoir.

Figure 1A:
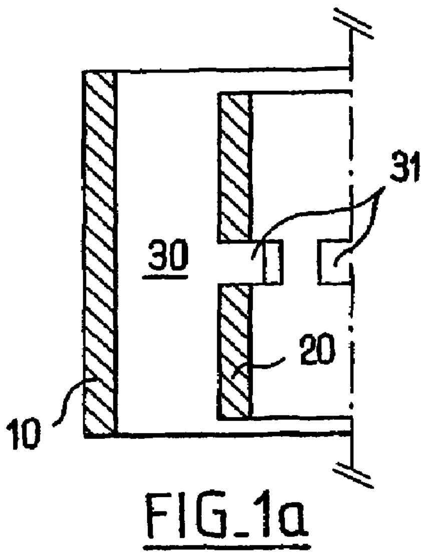
FIGS. 1*a* and 1*b* are half-sectional views of an annular reservoir.
Figure 1B:
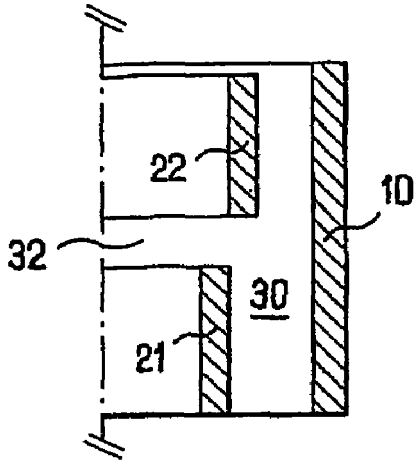

With reference to FIG. 1*a*, an annular reservoir 30 is at least limited by an internal tube 20 and an external tube 10, both tubes being substantially coaxial. For filling the annular reservoir 30, one 20 of the internal 20 and external 10 tubes has one or more orifices 31 passing through the thickness of the tube so as to place the reservoir 30 in communication with the outside. In the case illustrated in FIG. 1*a*, the orifices 31 are distributed uniformly over a circumference of the internal tube 20. With reference to FIG. 1*b*, it is possible to implement this type of orifice in a simple manner by replacing the internal tube described above with two internal tubes 21, 22 having different diameters. For example, the difference between the two diameters is of the order of one thickness of the smallest internal tube 21. The difference in diameter between these two internal tubes 21 and 22 thus creates an offset allowing slots 32, acting as orifices, to be made, at the level of the smallest internal tube 21, the number and length of arc of which may vary depending on the nature of the fluid containing the active principles to be administered (inter alia the viscosity) and the quantity. This configuration of the two internal tubes allows a simple, inexpensive manufacturing of the orifices, for example by means of a moulding process.

Figure 2A:
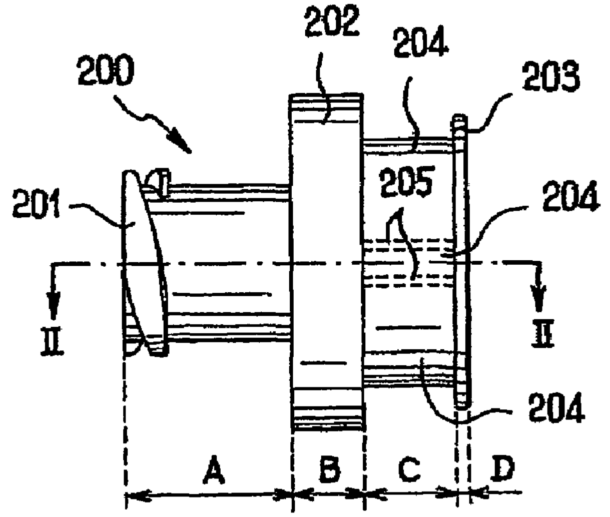
FIGS. 2*a* and 2*b* are a solid view and a sectional view along II-II of a first embodiment of a connector for feeding active principles according to the invention.
Figure 2B:
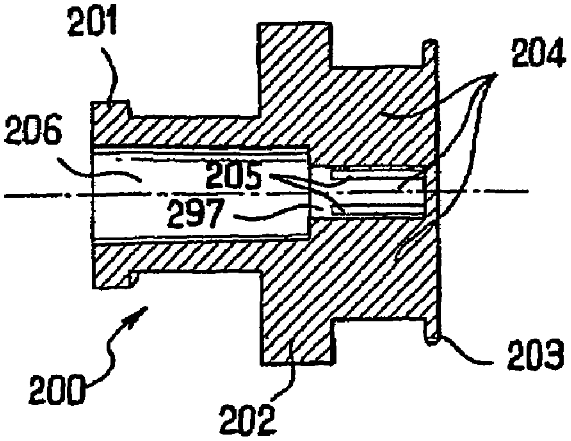

With reference to FIGS. 2*a* and 2*b*, we will describe an active-principle feed connector 200 for filling a reservoir as described above. The feed connector 200 includes four parts, which are described as follows:

- a "proximal connection" part A for presenting an interface with a receptacle containing the fluid to be transferred into the reservoir 30;
- a "proximal sealing" part B whose main role is to produce a seal with the internal tube 22 of largest diameter of the reservoir 30 described above. This produces an upstream seal;
- an administration part C arranged so as to be in connection with the orifices of the reservoir 30 described above; and
- a distal sealing part D whose main role is to produce a seal with the internal tube 21 of smallest diameter. This produces a downstream seal.

We will now describe these four parts in greater detail.

The proximal connection part A thus produces the interface with the receptacle containing the fluid with the active principles for administration. This part may have two general forms: either the fluid receptacle is removable or it is secured to the feed connector by means of the proximal connection part A.

In the case of the removable receptacle (such as a pre-filled syringe or a flexible bottle or, alternatively, a perfusion pipe or even a bellows-type bottle), the receptacle ends in an endpiece that may be standardized, such as a male Luer, or maybe a specific or proprietary device of the supplier of said fluid receptacle. In order to produce the connection, the proximal connection part includes means 206 for connection with this type of endpiece. Illustrated in FIG. 2*b*, these connection means 206 are a female Luer.

Figure 4A:
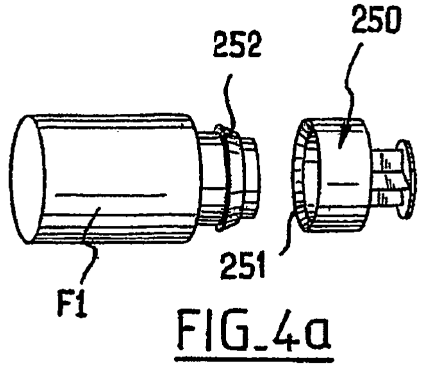
FIGS. 4*a* and 4*b* are variant embodiments of a feed connector according to the invention with a receptacle containing fluid to be dispensed.
Figure 4B:
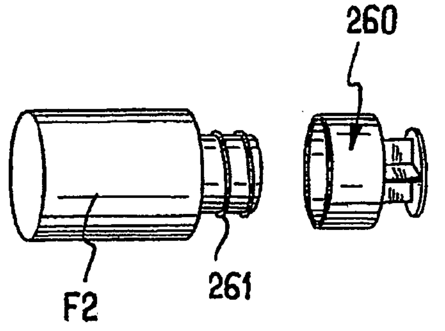

In the case of a fixed or secured fluid receptacle, the latter has integral linking means capable of interacting with complementary integral linking means 201 provided at the level of the proximal connection part A of the feed connector 200. In the case illustrated in FIGS. 2*a* and 2*b*, these integral linking means 201 are a screw thread located on the outside of said proximal connection part. Variant embodiments are illustrated in FIGS. 4*a* and 4*b*. In FIG. 4*a*, the fluid receptacle F1 has integral linking means 252 in the form of a lip of substantially cylindrical shape facing towards the rear part of the receptacle F1 whilst being spaced from the endpiece outwards. The feed connector 250 according to the invention has, in its proximal connection part A, integral linking means 251 that complement integral linking means 252 of the receptacle F1. Thus, the interconnection between the receptacle F1 and the feed connector 250 according to the invention takes place by means of a push-fit. In a second variant embodiment, illustrated in FIG. 4*b*, the fluid receptacle F2 is provided with integral linking means 261 in the form of an external screw thread capable of interacting with a complementary screw thread provided on the feed connector 260. The connection between the fluid receptacle F2 and the feed connector 260 in this case takes place by means of screwing.

Next, the main function of the proximal sealing part B is to provide the seal with the larger of the two internal tubes 22 of the reservoir 30 with which the feed connector 200 according to the invention is to interact. This proximal sealing part includes a cylinder 202 of substantially circular cross section. In a variant embodiment, the cylinder 202 is replaced by a frustum of a cone. Generally speaking, the height of this cylinder or of this frustum of a cone can vary. Moreover, it is possible to arrange at the rear of this proximal part, i.e. at the level of and/or opposite the proximal connection part A described above, a functional piece for fastening onto the reservoir, this functional fastening piece being similar, in principle, to that described below when we address the distal sealing part D.

Figure 5A:
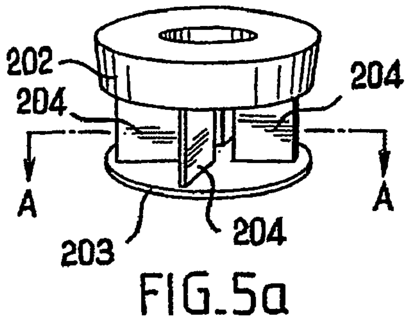
FIGS. 5*a* to 8*b* are variant embodiments of the part for administering active principles of a dispensing connector according to the invention.
Figure 5B:
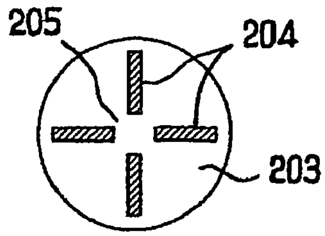
Figure 6A:
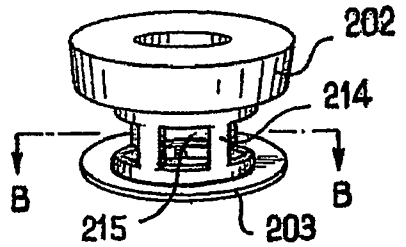
Figure 6B:
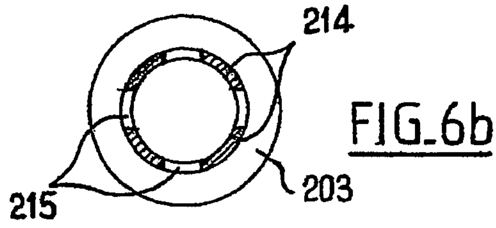
Figure 6C:
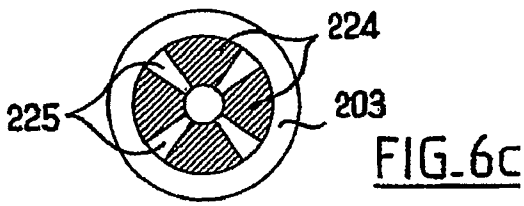

Next, the role of the administration part C is to uniformly supply the fluid for filling the reservoir 30 to the various orifices allowing filling of said reservoir 30. This administration part is in communication with the connection means 206 of the feed connector 200 by means of a conduit 297. The conduit 297, of substantially circular cross section, is arranged so as to be coaxial with the principal axis of the connector. In a first embodiment, illustrated in FIGS. 5*a* and 5*b*, the administration part C has spacing ribs or blades 204 extending between the proximal sealing part 202 and the distal sealing part D, here shown in the form of a circular plate 203 and described in greater detail below. The arrangement of the blades or ribs 204, which are four in number in this case, is such that they extend radially. The end facing the conduit 297 delimits passage orifices 205 between said conduit 297 and the outside of the connector 200. The other end, which faces the outside of said connector, ends so as to leave a space between said end and the edge of the plate 203. When the feed connector is fitted in the delivery device including the reservoir 30, this allows the edge of one of the blades of one of the through-orifices allowing filling of said reservoir 30 to be kept unobstructed. In a second variant embodiment, illustrated in FIGS. 6*a* and 6*b*, the administration part C has a series of apertures 215 made in a tube 214, the diameter of which is substantially greater than the diameter of the supply conduit 297 and substantially smaller than the diameter of the plate 203. The apertures 215 are uniformly distributed over the circumference of the tube 214. In another variant embodiment, illustrated in FIG. 6*c*, the tube 224 has a relatively large thickness, delimited by an internal diameter substantially equivalent to the diameter of the supply conduit 297 and by an external diameter substantially smaller than the diameter of the plate 203. The apertures 225 are arranged so as to allow the fluid to pass from the supply conduit 297 towards the outside.

Figure 7A:
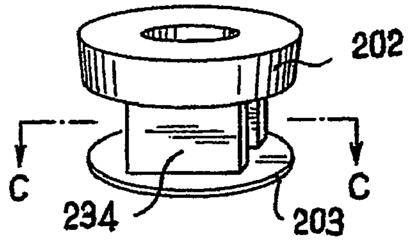
Figure 7B:
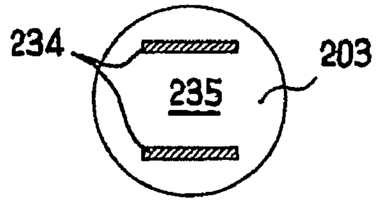
Figure 8A:
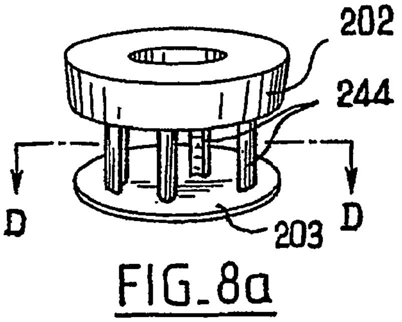
Figure 8B:
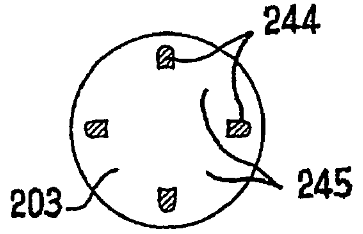

In another variant embodiment, illustrated in FIGS. 7*a* and 7*b*, the administration part C comprises at least two blades or ribs 234 that are parallel to one another, extending opposite to one another, thereby limiting at least one passage space 235 between the supply conduit 297 and the outside of the administration part C with a view to allowing the fluid to be injected into the reservoir 30 to pass. In another variant embodiment, illustrated in FIGS. 8*a* and 8*b*, the administration part includes a series of spacers 244 connecting the plate 203 with the cylinder 202. The spaces 245 between the various spacers allow the passage of fluid. The spacers 244, which are four in number in this case, are uniformly distributed substantially over a circle, the diameter of which is smaller than the diameter of the plate 203 and larger than the diameter of the supply conduit 297.

All these variant embodiments make it possible to provide at least one embodiment solution for the administration part adapted to a given fluid, depending on its quantity and viscosity among other elements to be taken into account when making this part.

Furthermore, the arrangement of the administration part is such that the fluid volume contained by said administration part is minimized relative to the volume actually introduced into the reservoir. This fluid volume contained by the administration part is called the "dead volume", and depends on:

the dimensions of the plates 202 and 203;

the space between said two plates;

the dimensions of the means forming the spacer 204, 214, 224, 234, 244 separating said two plates; and the properties of the fluid to be administered.

In a practical manner, for example in the case of an annular reservoir having an internal diameter greater than 50 mm and a thickness of the order of 5 mm the dead volume of the administration part becomes greater than the volume to be administered into the reservoir.

Figure 3A:
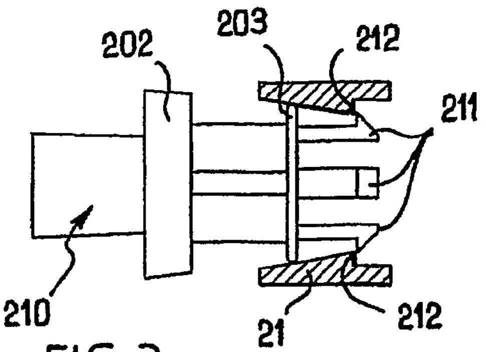
FIGS. 3*a* to 3*d* are variant embodiments of links between the feed connector according to the invention and an active-principle reservoir.

Lastly, the distal sealing part D is located to the front of the feed connector 200 and produces a seal between said connector and the internal tube 21 of smallest diameter delimiting the reservoir 30. The height of the distal sealing part D may vary. Illustrated in FIGS. 2*a* and 2*b*, and also in FIGS. 5*a* to 8*b*, the distal sealing part D comprises a thin plate 203 of substantially circular cross section. In a variant embodiment, this plate may have a concavity and/or a convexity. Moreover, it is possible to arrange, to the front of this plate and generally of the distal sealing part, a functional piece for temporary or definitive fastening or catching onto the reservoir. Such possibilities in the variant embodiments are illustrated in FIGS. 3*a* to 3*d*. FIG. 3*a* shows a push-fit fastening system, and the internal tube 21 of the reservoir 30 has a lip 212 extending as a projection radially towards the axis of said internal tube 21 and capable of interacting with tongues 211 extending as a projection towards the front of the plate 203 of the feed connector 210. This allows push-fit fastening of said feed connector 210 on the reservoir 30.

Figure 3B:
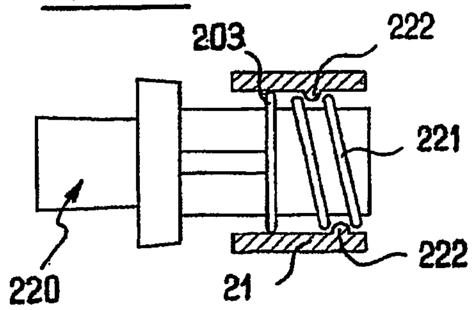
Figure 3C:
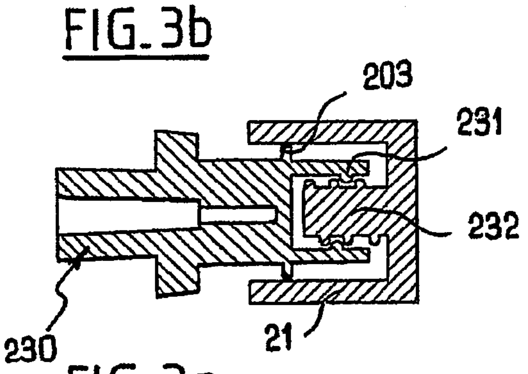

FIG. 3*b* illustrates, for the feed connector 220, a variant fastening by means of a screw thread 221 provided on the external surface of a cylindrical projection of substantially circular cross section extending to the front of the plate 203 and capable of interacting with a complementary screw thread 222 provided on the internal face of the tube 21 of the reservoir 30. A variant embodiment, illustrated in FIG. 3*c*, is the reverse of that illustrated in FIG. 3*b* in that the internal tube 21 includes, coaxially, a projection 232 of circular section having, on its outer face, a screw thread capable of interacting with a complementary screw thread 231 provided in a tube extending as a projection to the front of the plate 203 of the feed connector 230.

Figure 3D:
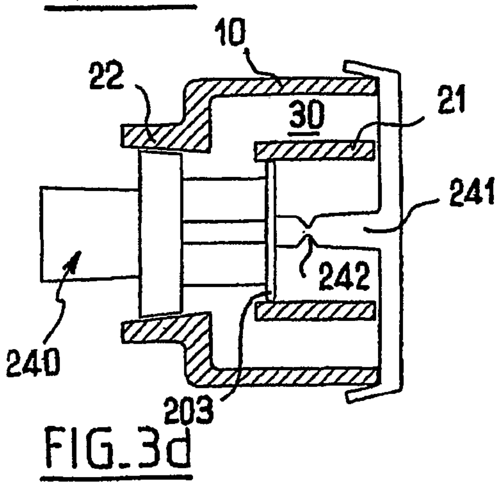

In another variant embodiment, illustrated in FIG. 3*d*, there is, to the front of the distal sealing part, a cover 241 capable of advantageously covering the open part of the reservoir 30 described above, thereby protecting it from the outside during the operation of filling said reservoir (protection from contamination, for example). This cover is fastened to the feed connector 240 by a rod joining the cover 241 to the plate 203 and having, at a location along its length, a more fragile part 242 that is capable of breaking under a mechanical action at the time the feed connector 240 is disconnected.

Figure 10:
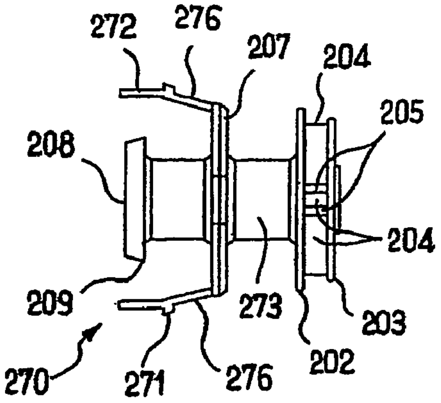
FIG. 10 is a side view of an active-principle feed connector according to a preferred embodiment of the invention.
Figure 11A:
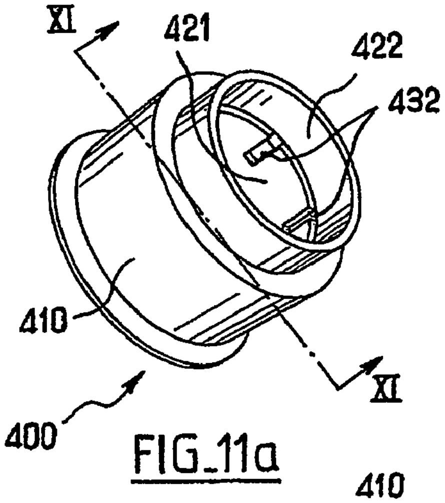
FIGS. 11*a*, 11*b* and 11*c* are a three dimensional view, a sectional view along XI-XI of the working part and a three-dimensional view, respectively, of a device for delivering active principles containing a reservoir capable of being filled by the feed connector of FIG. 10.
Figure 11B:
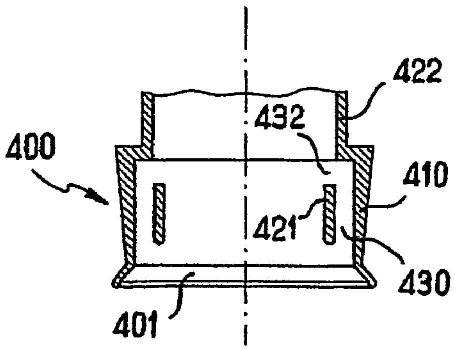
Figure 11C:
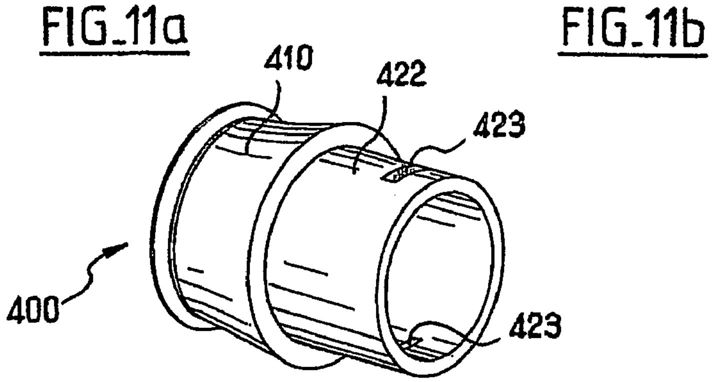

With reference to FIG. 10, we will describe a preferred embodiment of a connector 270 for feeding fluid containing active principles according to the invention. The feed connector 270 is a connector very similar to the connector 200 described above in that the proximal sealing part B, the administration part C and the distal sealing part D are similar. The proximal connection part A includes a cylinder 273 of substantially circular cross section attached at a first end to the plate 202 acting as proximal sealing part B. The opposite end 208 comprises retention means 209 that extend as a projection from the periphery of the cylinder 273 so as to form a retention lip facing the distal part of the feed connector 270. Furthermore, the cylinder 273 comprises, located substantially coaxially, an orifice of frustoconical shape acting as connection means 206 described above. Substantially midway between the two ends of the cylinder 273, the feed connector 270 includes a plate 207 of essentially circular shape, at the periphery of which extend, as projections, catching tongues (delivery-device fastener) 276, which are two in number in this case, distributed uniformly over said periphery. Each of the catching tongues 276 includes at least one stud 271 extending as a projection centrifugally, and also implementation means 272 in the form, here, of a lever extending the tongue.

Figure 9:
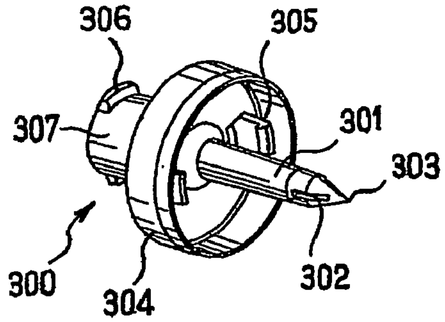
FIG. 9 is a three-dimensional view of a striker to be fitted onto an active-principle receptacle and for cooperating with a feed connector of FIG. 10 according to a preferred embodiment of the invention.

With reference to FIG. 9, we will describe a striker (fluid-receptacle interface connector) 300 capable of being used with the feed connector 270 described above. The striker 300 has connection means 301 provided with orifices 302 at a distal end. The distal end ends in a point 303. The connection means 301 are of frustoconical shape, complementing the frustoconical shape of the connection means 206 of the feed connector 270 described above. This complementarity makes it possible to provide a sealed connection during fitting of the striker 300 onto the feed connector 270. The striker 300 also includes an "offset" ring (delivery-device disengagement member) 304 capable of interacting with the implementation means 272 of the catching tongues 276 of the feed connector 270. The striker 300 also includes catching means (feeds connector fastener) 305, in this case in the form of tongues extending as a projection towards the distal part of the striker of the ring 304. These catching means 305 are capable of interacting with the lip 209 of the feed connector 270 so as to securely fasten said striker 300 to said feed connector 270. Furthermore, the striker 300 includes a proximal connection part 307, in this case of cylindrical shape and substantially circular cross section, extending as a projection in a proximal manner from the ring 304. At a proximal end, the striker 300 has fastening means 306 that in this case are in the form of screw-thread parts and also a standardized female Luer extending internally via a channel opening out at the orifices 302 so as to allow the passage of the fluid from any receptacle capable of being fastened onto the proximal connection part 307 of the striker 300 and containing the fluid to be injected into a reservoir of a delivery device that we will describe below.

With reference to FIGS. 11*a*, 11*b*, 11*c* and 12*c*, we will describe a medicinal-product delivery device capable of being used with the feed connector 270 described above. The delivery device 400 includes a working part 401 capable of being fitted over the tissues that are to receive the active principles contained in a reservoir 430 of said delivery device 400. The reservoir 430 is delimited externally by an external tube 410 and internally by an internal tube 421 substantially coaxial with the external tube 410. At the top of the reservoir 430, an internal tube 422 with a diameter greater than the internal tube 421 extends as a projection so as partially to close the reservoir 430. The reservoir 430 has, at its top, a series of orifices 432 uniformly distributed over the circumference of the internal tube 421. In this case, these orifices are six in number. Lastly, the internal tube 422 has through-orifices 423, which are two in number in this case, uniformly distributed over a circumference of said tube 422 and capable of interacting, as we will see below, with the studs 271 of the feed connector 270. The delivery device 400 described here is for application to an eyeball. The reservoir 430 for receiving the fluid has the form of a ring including an internal tube 421 with a minimum diameter of approximately 10 mm and an external tube 410 with a maximum diameter of approximately 25 mm. The space between these two tubes is of variable thickness (gap, depending on the thickness of the walls of said tubes, but is typically between approximately 14 mm and 17 mm in diameter). This space forming the reservoir 430 is closed at one end and open at the other end. The length of the internal tube 421 can also vary, but is between approximately 1 mm and 10 mm. If appropriate, said reservoir 430 may contain an absorbent material for holding the liquid in place until it is used, i.e. up until transfer of the active principles into the ocular tissues. The absorbent material may be foam, hydrogel or fibres.

Figures 12A, 12B, 12C:
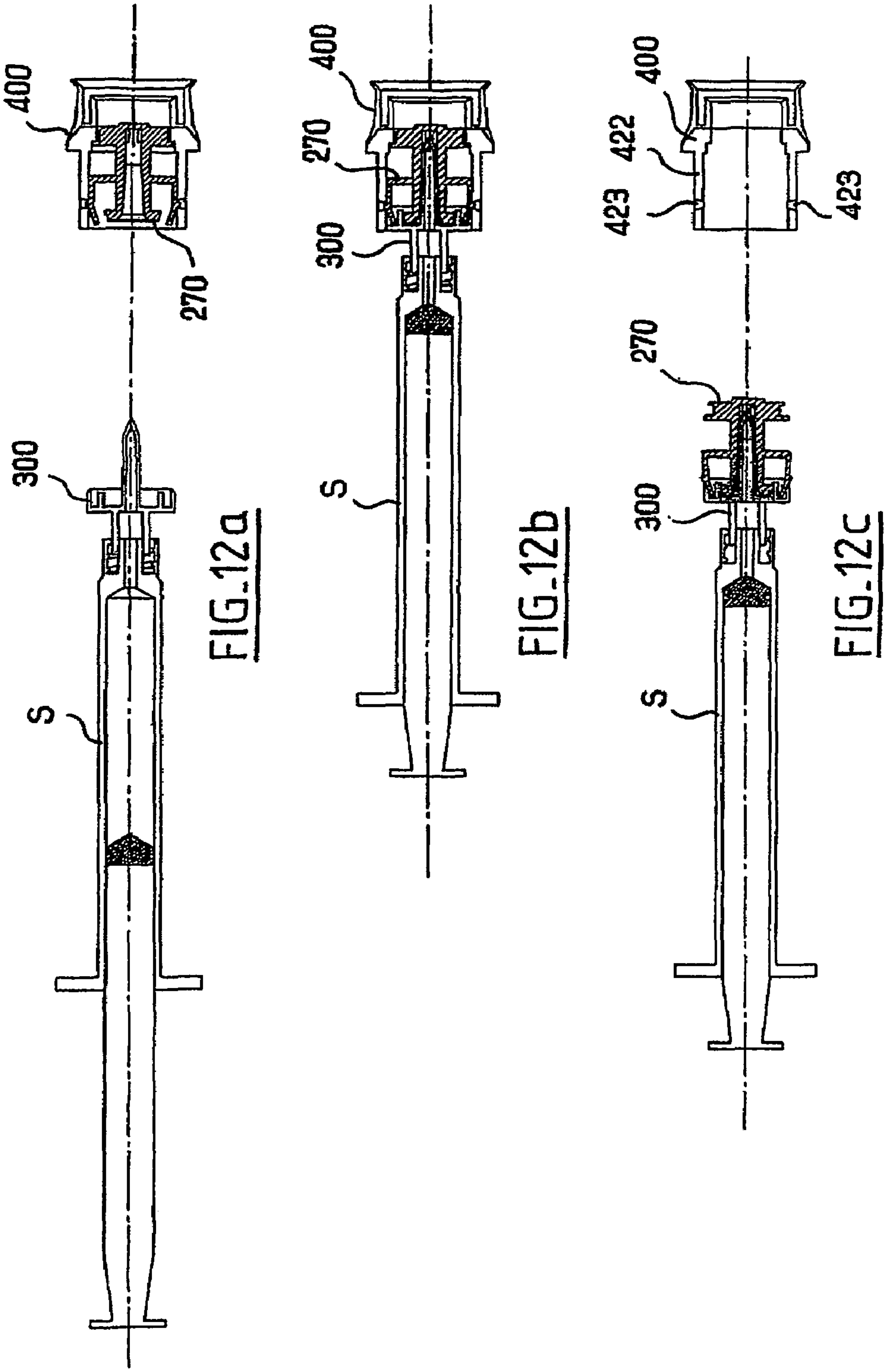
FIGS. 12*a*, 12*b* and 12*c* illustrate the steps in the implementation of an active-principle feed connector according to the invention of FIG. 10.

With reference to FIGS. 12*a*, 12*b* and 12*c*, we will describe an implementation of the feed connector 270 according to the invention described above. Firstly, the receptacle S containing the fluid, in this case a syringe, is securely connected to the proximal part of the striker 300 with the aid of the fastening means 306 of the striker 300 interacting with the complementary connection means of the syringe S. The use of such a striker 300 makes it possible, if desired, to produce a mix so as to prepare the fluid containing the active principles for injection into the reservoir 430 of the delivery device 400. To that end, the striker 300 is next clamped onto the connector 270 pre-installed in the delivery device 400, as illustrated in FIG. 12*a*. When the feed connector 270 is installed in the delivery device 400, as we have described above, the distal sealing part interacts in a sealing manner with the internal wall of the internal tube 421. The administration part extends opposite the uniformly distributed orifices 432 of the reservoir 430. The proximal sealing part operates in a sealing manner with the internal wall of the tube 422, whilst the studs 271 interact with the through-orifices 423 of the internal tube 422 so as to secure the feed connector 270 to the delivery device 400. During fitting of the striker located at the end of the syringe S into the feed connector 270, the disengagement ring 304 comes to bear on the levers 272, elastically deforming all the catching tongues 276 so as to disengage the studs 271 from the through-orifices 423. Practically simultaneously, the catching tongues 305 of the striker 300 interact with the circular lip 209 of the feed connector 270, thus securely fastening the striker 300 onto the feed connector 270. All that then remains to be done is to inject the fluid contained in the receptacle S into the reservoir 430. At the end of that operation, the configuration illustrated in FIG. 12*b* will be achieved. Once the reservoir 430 has been filled, the receptacle F is removed. During this removal, it entrains the striker 300 to which it is securely fastened and the striker brings with it the feed connector 270 to which it in turn is securely fastened by virtue of the catching tongues 305 interacting with the circular lip 209. The fact that, once the fluid has been injected, the feed connector 270 has to be removed makes it possible to guarantee a single use of the active-principle delivery device 400. Indeed, it is customary and even mandatory, since the taking into account of the risks of cross-contamination between patients or between patients and care staff, that any medical device should be used only once for a given patient, as confirmed by the development of "single-use" equipment that is sold sterile and disposed of after use. However, despite this "single-use" indication affixed to this type of medical device, there is nothing to prevent such devices actually being reused on a number of patients. Hence the embodiment described above that makes it possible to guarantee that the active-principle delivery device 400 cannot be used more than once, given that once the dispensing connector 270 has been removed it is no longer possible to fill the reservoir 430 of the delivery device 400. Similarly, it is impossible to reuse the striker 300 because this is secured to the feed connector 270 then serving as protector with a view to preventing any risk of contamination by accidental needle stick.

The advantages of a feed connector 270 described above are:

- to allow administration, while minimizing dead-volume losses as much as possible, of a viscous or non-viscous fluid uniformly distributed in the reservoir of a medical delivery device;
- to secure the feed connector to the medical device, thereby preventing its normal use unless this piece can be removed;
- to propose a striker that can be connected to the feed connector, transfer the fluid for administration into the reservoir of the delivery device and then disconnect the feed connector from said delivery device; and
- to effectively secure the striker and the feed connector together so as to prevent their reuse.

Naturally, a number of modifications may be made to the invention without thereby departing from its scope.

In particular, the reservoir may have any shape depending on the intended use of the active-principle delivery device. Generally speaking, the reservoir may be limited by at least two lateral walls of substantially cylindrical shape extending opposite one another. At the very least, the shape of the administration part C then follows one of these walls to provide as uniform filling of the reservoir as possible.

The invention claimed is:

1. A device for delivering active principles, the device comprising:

an outer wall and an inner wall forming an annular reservoir therebetween, the walls of substantially cylindrical shape; and a feed connector for transferring the active principles from a fluid receptacle to the annular reservoir comprising:

means for dispensing the active principles into the reservoir that are arranged such that said reservoir is filled substantially uniformly between the inner and outer walls, wherein the annual reservoir is configured to deliver the active principles to ocular tissues of an eye.

2. The device according to claim 1, characterized in that the dispensing means comprise distribution means capable of distributing the active principles substantially uniformly before they arrive in said reservoir.

3. The device according to claim 2, characterized in that the distribution means have two plates spaced apart from one another and extending opposite one another, thereby delimiting a space for distribution of the active products.

4. The device according to claim 3, characterized in that the plates are held apart and secured to one another by means forming a spacer.

5. The device according to any one of the preceding claims, characterized in that the dispensing means are capable of filling the reservoir substantially radially through orifices made in one of the two lateral walls.

6. The device according to claim 1, characterized in that the dispensing means comprise a conduit for supplying the active principles.

7. The device according to claim 1, characterized in that the feed connector also includes means for connection with a receptacle containing the active principles for filling the reservoir.

8. The device according to claim 7, characterized in that the connection means are arranged such that, once the connection has been made between the receptacle and the connector, said connection is practically irreversible.

9. The device according to claim 1, characterized in that it also includes locking means capable of locking said connector in place once said connector is interacting with the device for delivering active principles.

10. The device according to claim 9, characterized in that the locking means are arranged so as to be practically disengaged during filling of said reservoir.

11. The device according to claim 10, characterized in that the locking means are arranged so as to be disengaged when the connection with the receptacle containing the active principles is made.

12. The device according to claim 9, characterized in that the locking means include at least one catching tongue capable of deforming elastically.

13. The device according to claim 12, characterized in that the locking means include at least one stud extending as a projection from the catching tongue and capable of interacting with an orifice made in the delivery device.

14. The device according to claim 1, characterized in that the dispensing means are arranged such that a ratio of the dead volume of the connector to a volume of the reservoir is minimal.

15. The device according to claim 1, further comprising at least one lever pivoting at about a distal point of attachment to the feed connector and configured to engage the annular reservoir for removably fastening the feed connector to the annular reservoir, wherein the feed connector is capable of interacting with the annular reservoir.

16. A fluid transfer system comprising:

a feed connector comprising feed-connector retaining means and at least one delivery-device fastener configured to engage an active principal delivery device in an interlocking arrangement;

a fluid-receptacle interface connector comprising at least one feed-connector fastener configured to engage the feed-connector retaining means in an interlocking arrangement allowing fluid transfer therethrough and with the active principal delivery device when so connected, the fluid-receptacle interface connector further comprising an integral delivery-device disengagement member, the integral delivery-device disengagement member disengaging the at least one delivery-device fastener from the active principal delivery device when the at least one feed-connector fastener has engaged the feed-connector retaining means, thereby allowing separation of the interconnected feed-connector-fluid-receptacle-interface connector from the active principal delivery device.

17. The fluid transfer system of claim 16, wherein the feed connector further comprises a distal end in fluid communication with an axial lumen configured to substantially uniformly supply a radial fluid flow to fill an annular reservoir of the active principal delivery device.

18. The fluid transfer system of claim 16, wherein the at least one delivery-device fastener comprises a flexible lever having a stud, the flexible lever biased to urge the stud against a suitably placed notch disposed along the active principal delivery device.

19. The fluid transfer system of claim 16, wherein the at least one feed-connector fastener comprises a push-fit fastener configured to securely engage the feed-connector retaining means when the feed-connector is interconnected to the fluid-receptacle interface connector.

20. The fluid transfer system of claim 16, wherein the fluid-receptacle interface connector includes means for fastening the fluid-receptacle interface connector to a fluid receptacle.

21. The fluid transfer system of claim 16, wherein a distal portion of the fluid-receptacle interface connector comprises a piercing tip and at least one fluid aperture disposed relative to the piercing tip providing fluid access to an axial lumen of the fluid-receptacle interface connector.

* * * * *